United States Patent [19]

Netherton et al.

[11] Patent Number: 4,900,309
[45] Date of Patent: Feb. 13, 1990

[54] NEEDLE SHIELD

[75] Inventors: Fred Netherton, 4250 Roseland Drive, W., Windsor, Ontario, Canada, N9G 1Z9; Steven Z. Livneh, 5120 Halford Drive, R.R. #1, Windsor, Ontario, Canada, N9A 6J3

[73] Assignees: Fred Netherton et. al; Windsor, Canada

[21] Appl. No.: 201,533

[22] Filed: Jun. 2, 1988

[51] Int. Cl.⁴ ............................................. A61M 5/00
[52] U.S. Cl. ..................................... 604/192; 604/263
[58] Field of Search ........................ 604/187, 192, 263

[56] References Cited

U.S. PATENT DOCUMENTS

| | | |
|---|---|---|
| 600,449 | 3/1898 | Richardson . |
| 1,179,560 | 4/1916 | Reed . |
| 2,550,394 | 4/1951 | Young et al. . |
| 2,661,740 | 12/1988 | Hickey . |
| 2,735,428 | 2/1956 | Huber . |
| 2,735,429 | 2/1956 | Huber . |
| 2,772,677 | 12/1956 | Ulert et al. . |
| 2,954,029 | 9/1960 | Metten . |
| 3,021,942 | 2/1962 | Hamilton . |
| 3,072,120 | 1/1963 | Sharp et al. . |
| 3,108,591 | 10/1968 | Kolbas . |
| 3,115,875 | 12/1968 | Wilburn . |
| 3,375,825 | 4/1968 | Keller . |
| 3,401,693 | 9/1968 | Cohen . |
| 3,920,001 | 11/1975 | Edwards . |
| 4,009,716 | 3/1977 | Cohen . |
| 4,270,536 | 6/1981 | Lemelson . |
| 4,445,895 | 5/1984 | Margulies . |
| 4,559,042 | 12/1985 | Votel . |
| 4,573,975 | 3/1986 | Frist et al. . |
| 4,623,336 | 11/1986 | Pedicano et al. . |
| 4,636,201 | 1/1987 | Ambrose et al. ................... 604/192 |
| 4,654,034 | 3/1987 | Masters et al. . |
| 4,742,910 | 5/1988 | Staebler ............................. 604/192 |
| 4,781,697 | 11/1988 | Slaughter ........................... 604/263 |
| 4,840,618 | 6/1989 | Marvel ........................... 604/192 X |

FOREIGN PATENT DOCUMENTS

| | | | |
|---|---|---|---|
| 3433359 | 4/1986 | Fed. Rep. of Germany ...... 604/192 |
| 2586568 | 3/1987 | France ................................ 604/263 |
| 85/03006 | 7/1985 | PCT Int'l Appl. ................. 604/192 |

*Primary Examiner*—John D. Yasko
*Attorney, Agent, or Firm*—Harness, Dickey & Pierce

[57] ABSTRACT

A shield for a hypodermic needle cover comprising a generally flat surface with a central opening permitting the needle cover to be inserted therein, and a locking means to prevent the shield from being removed. The shield is rigid and includes a rim which surrounds the central opening for preventing the hypodermic needle froms slipping off the edge of the shield during insertion.

12 Claims, 2 Drawing Sheets

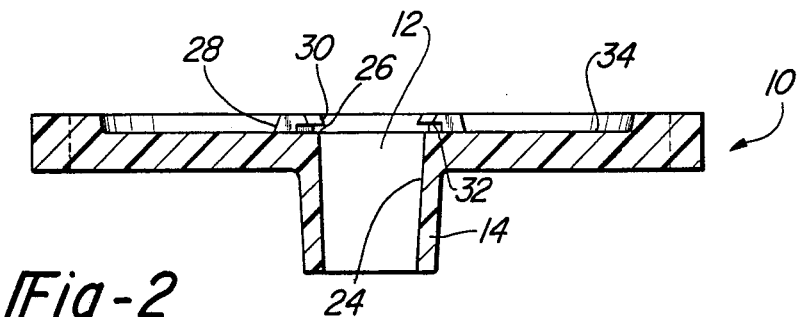
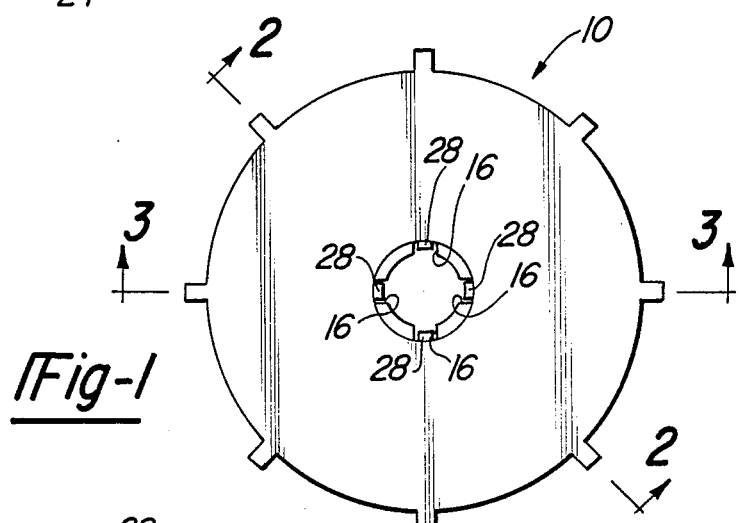
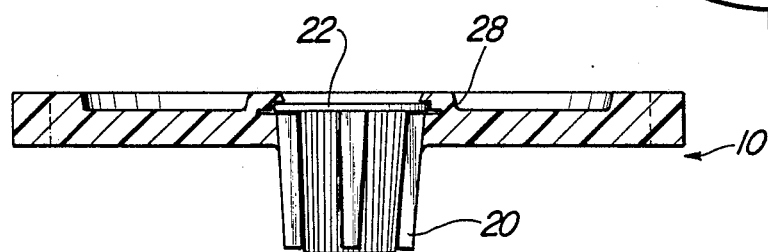
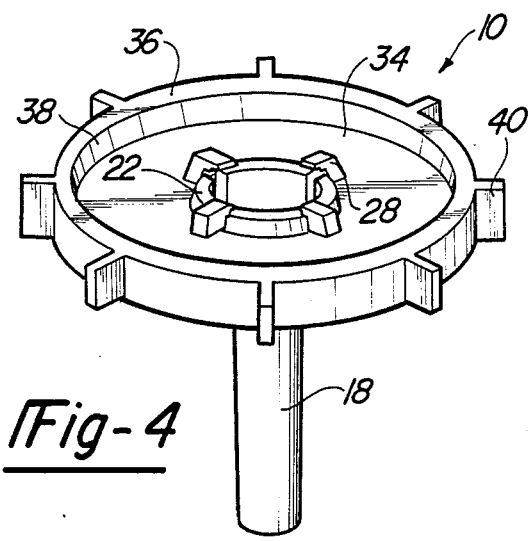

NEEDLE SHIELD

BACKGROUND AND SUMMARY OF THE INVENTION

Conventional hypodermic needle covers comprise small diameter tubular coverings with an opening at one end for receiving a needle. These needle cover are placed over the needle when hypodermic syringes are first assembled to keep them sterile. The same needle cover may also be used to cover the needle after the hypodermic needle has been used. It has long been a problem that persons inserting needles into the needle covers accidentally miss the needle cover opening and stick themselves with the needle. This is a serious problem because a number of serious diseases including hepatitis and AIDS are known to be spread in this way. Thus, it is important for persons using hypodermic needles not only to avoid direct contact with the needle, but also for them to avoid being in close proximity to an unsterile used needle.

In response to these problems, some efforts have been made to develop safety shields for hypodermic needles. These include U.S. Pat. Nos. 4,654,054, 4,573,975 and 4,623,336. The structures disclosed in these references provide some protection over conventional needle covers by means of new needle cover designs incorporating various kinds of shields. However, due in part to the complexity and cost of these special needle covers, they have not been widely employed. In addition, these shields, when inserted on an unused hypodermic syringe, make the total syringe package excessively bulky.

One partial solution is to use a sheild which attaches to a conventional standard needle cover. In this way, the cost of the shield is minimized because existing low cost, mass-produced needle covers may still be used with the shield. Also, if the shield is attached to the needle cover only after the syringe has been used, the problem of adding bulk to the unused hypodermic package would be eliminated. One example of such a structure is found in U.S. Pat. No. 4,559,042. However, a number of problems still are present with the type of shield disclosed in this, as well as other patents. First, while most shields provide some protection against accidental sticking, there is still the possibility of a needle slipping off the shield during insertion. This can occur because if the needle misses the central opening of the needle cover and strikes the shield on one side, the resulting of-axis torque is likely to cause the needle cover to tilt in the user's hand. During the attempted insertion, this tilting can result in the needle slipping off the shield where it may strike the user's fingers, hands or arms that are not directly behind the shield. While simply making the shield much larger is one possible solution, as a practical matter, the diameter of the shield must be kept to a reasonably small size. In addition, a number of previous shields are flexible and this flexibility may also contribute to the needle slipping off the edge of the shield.

An additional problem with prior needle shields that are designed to be used with conventional needle covers, is that the shield can be removed from the needle cover. Removability opens the possibility of medical personnel reusing the same shield with a different needle cover. Because the shield may have had contact with the first needle and also because in the process of removing the shield the needle cover may be removed and the needle exposed, there is a chance of infection when the needle shield is removed from the needle cover.

The present invention improves upon previous needle shields by providing a needle shield that can be attached to a standard needle cover. The present invention also provides a needle shield with a means for locking the needle cover onto it so that the needle shield cannot be removed. The shield is rigid and also provides a rim for preventing the needle from sliding off the edge of the shield during insertion.

Accordingly, it is a general object of the present invention to provide a new and improved hypodermic needle shield. It is a more particular object of the present invention to provide a hypodermic needle shield which is simple, low-cost and can be used with a conventional needle cover. It is yet another object of the present invention to provide a hypodermic needle shield that cannot be removed from the standard needle cover and reused. It is still a further object of the present invention to provide a hyprodermic needle shield that is rigid, small enough to be of practical use, yet effective in preventing the needle from slipping off the edge of the shield when the needle strikes the shield on one side during an attempted insertion of the needle into the needle cover.

Additional objects and advantages of the present invention will become apparent from the following detailed description taken in conjunction with the accompanying claims.

BRIEF DESCRIPTION OF THE DRAWINGS

FIG. 1 is a bottom plan view of the needle shield in accordance with the present invention.

FIG. 2 is a side elevational view in cross section of the needle shield along lines 2—2 in FIG. 1.

FIG. 3 is a side elevational view partially in cross section of the needle shield along lines 3—3 in FIG. 1 with a conventional needle cover installed in accordance with the present invention.

FIG. 4 is a perspective view of the needle shield with a needle cover installed in accordance with the present invention.

DETAILED DESCRIPTION OF THE PREFERRED EMBODIMENTS

Figure 5:
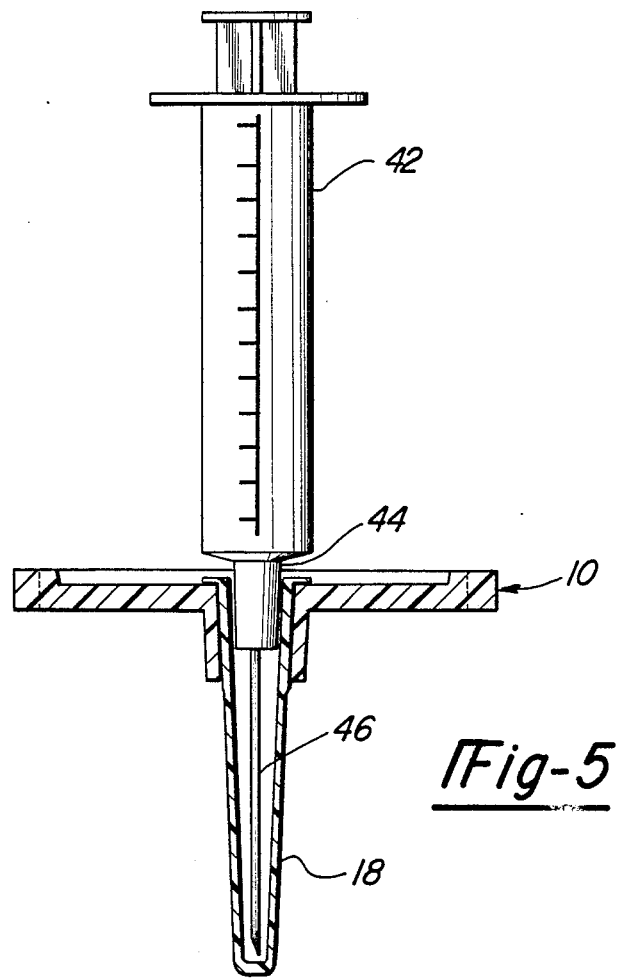
FIG. 5 is a side elevational view partially in cross section of the needle shield with a needle cover installed and also with a hypodermic syringe inserted into the needle cover, in accordance with the present invention.

Referring now in detail to the drawings and, in particular to FIGS. 1 and 2 thereof, the needle shield 10 is shown comprising a planar disc-shaped member having a central opening 12. A bottom reinforcing hub 14 extends downward around the central opening 12. The bottom hub 14 serves to strengthen and reinforce the needle shield 10 to prevent bending of the shield 10. The inner diameter of the bottom hub 14 is tapered and is slightly larger than the outer diameter of a standard hypodermic needle cover. The bottom hub 14 also has four slots 16 extending axially along its length. As shown in FIG. 3, a standard hypodermic needle cover 18 has a tapered outer diameter which conforms to the inner diameter of the bottom hub 16. The needle cover 18 also has fin portions 20 extending axially along it length, and a flange 22 at the open end.

The central opening 12 of the needle shield 10 has an inner wall 24, which is slightly larger than the outside diameter of the needle cover 18. This wall 24 is formed by the inner diameter of the bottom hub 14. At the top of the central opening 12 there is formed a ledge or seat 26 upon which the flange 22 rests when the needle cover 18 is inserted into the central opening 12.

In order to permanently secure the needle shield 10 to the needle cover 18, one or more retaining tabs 28 are provided, extending partially in a cantilevered fashion radially inward above the central opening 12. As shown in FIG. 1, there are four retaining tabs 28. As shown in FIG. 2, each retaining tab 28 has an angled surface 30 and a horizontal surface 32. The angled surface 30 engages with the flange 22 when the needle cover 18 is inserted downward into the central opening 12. Downward pressure by the flange 22 on the angled surface 30 creates radial forces on the tabs 28, causing the tabs 28 to move out of the way and permitting the flange 22 to move past the tabs 28 until the flange 22 rests on the seat 26 above the central opening 12. In this way, the flange 22 is permanently secured between the seat 26 and the horizontal surface 32 of the tabe 28. If an attempt is made to remove the needle shield 10 from the needle cover 18 by moving the needle cover 18 in an upward direction, the horizontal surface 32 of the tab 28 will prevent upward motion. If extreme forces are used, rather than bending, the tab 28 will break and render the needle shield 10 effectively unusable.

As shown in FIG. 4, the shield 10 also has a substantially flat base 34 extending radially outward from the central opening 12. The base 34 is made of a rigid material of sufficient thickness so that it is not easily bent. The diameter of the base 34 is substantially larger than that of the flange 22, thus providing significant protection to the user during insertion of a hypodermic needle. The larger the diameter of the base 34, the better the protection to the user, from accidental sticking. As a practical matter, however, if the base 34 is too large, the shield will become expensive and cumbersome to use. A diameter of about two inches has been found to be a workable size.

At the outer perimeter of the base 34 there is a rim guard 36 having an inner wall 38 extending upward from the base 34. While the rim guard 36 serves as an additional reinforcement to strengthen the shield 10 and prevent the base 34 from flexing, it also acts as a guard to prevent a needle from slipping off the shield 10 during insertion. If the user attempts to insert a needle into the central opening 12 and misses, the needle will likely strike the base 34. This will cause off-axis forces to be exerted on the needle cover 18, and may cause the needle cover 18 to tilt in the user's hand. This may allow the needle to slide toward the edge of the base 34. Consequently, without the rim guard 36, the needle may slip completely off the shield 10 and strike the user on a part of the hand or arm that is unprotected by the shield 10. On the other hand, with the rim guard 36, the needle will be caught by the surface 38 of the rim guard 36 and will be safely confined therein.

Also shown in FIG. 4 are a number of ribs 40 extending radially outward from the outer perimeter of the rim guard 36. These ribs 40 prevent the assembled needle shield 10 and needle cover 18 from rolling when placed on a flat surface. The ribs 40 also facilitate gripping the needle shield 10 during insertion of the needle cover 18 onto the needle shield 10. It will be appreciated that other means may be employed to prevent rolling, for example, the shield may be provided with an outer perimeter having a shape other than circular.

Figure 6:
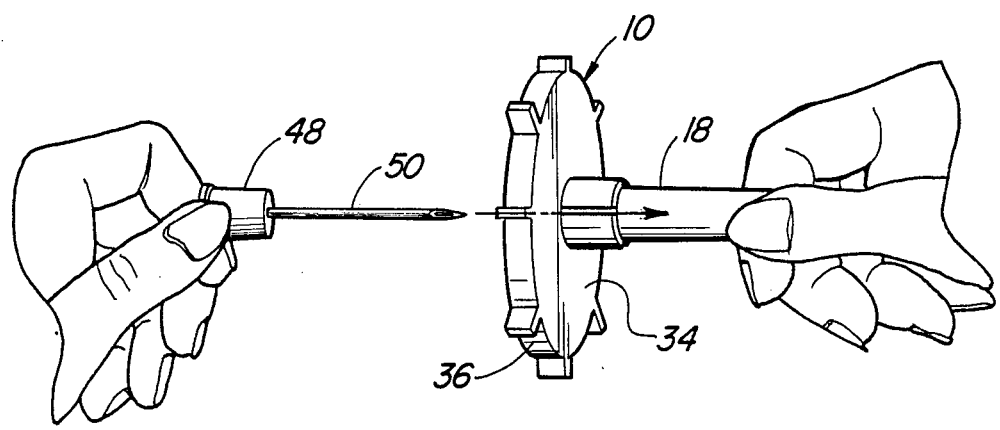
FIG. 6 is a perspective view of the needle shield with the needle cover installed illustrating the process of insertion of a needle by a user in accordance with the present invention.

Once the needle cover 18 has been inserted into the central opening 12 of the needle shield 10 and locked in place by the tabs 18, it is ready for the insertion of a hypodermic needle. In FIG. 5, there is shown a hypodermic syringe 42 having a needle hub 44 and a hypodermic needle 46, after the hypodermic syringe 42 has been inserted into the needle shield 10 and the needle cover 18. The inner diameter of the needle cover 18 matches the size and shape of the outer diameter of the needle hub 44, so that a moderate amount of pressure causes the needle cover 18 to be tightly secured to the needle hub 44. Where the syringe 42 is of the disposable type, the entire assembly comprising the syringe 42, the needle shield 10 and the needle cover 18 is disposed of after use. In nondisposable syringes, however, the needle hub 44 may first be removed for disposal. This type of needle hub 48 is shown in FIG. 6. To properly insert the needle hub 48 and the needle 50 into the needle cover 18, the needle hub 48 is held in one hand and the needle cover 18 is held in the other hand, as shown in FIG. 6. The needle 50 is then inserted into the needle cover 18 until the hub 48 is snugly seated within the needle cover 18. It can be seen that the needle shield 10 provides an effective means for preventing accidental sticking with the needle 50 during insertion. Should the user miss the central opening 12 in the shield 10, the base 34 and the rim guard 36 will effectively confine the needle within the needle shield 10.

It will be appreciated that the needle cover 18 is one of many types of needle covers in common use. The needle shield 10 in accordance with the present invention can be easily fabricated to be used with other types of needle covers, simply by matching the dimensions of the central opening 12 and the bottom hub 16 to those of the needle cover. While it is apparent that the preferred embodiments of the invention disclosed are well calculated to fulfill the objects of the invention, it will be appreciated that the invention is susceptible to modification, variation and change, such as the use of a noncircular shield, or other changes without departing from the proper scope or fair meaning of the subjoined claims.

We claim:

1. A protective shield for use with a hypodermic needle comprising:
    a tubular needle cover having an open end for receiving said needle and having a flange near the open end;
    a generally planar and rigid shield means having a central opening for receiving said tubular needle cover, and having a planar surface perpendicular to the longitudinal axis of the tubular needle cover; and
    means for permanently fastening said flange within said central opening when said tubular needle cover is inserted into said central opening comprising
    a portion of said central opening having a smaller diameter than said flange, wherein said planar surface forms a seat that contacts the bottom surface of said flange when said needle cover is inserted into said central opening; and
    at least one moveable tab member extending from said planar surface partially over said central opening, for engaging the top surface of the flange when the bottom surface of the flange is positioned over said seat.

2. The invention as set forth in claim 1 further comprising a series of protruding portions extending radially outward from the perimeter of said shield for preventing said shield from rolling when placed on a flat surface.

3. The invention as set forth in claim 1 wherein said tab member has an angled portion which contacts the bottom of said flange portion when said needle cover is being inserted into said central opening for facilitating movement of said tab member; said tab member also having a flat surface parallel and adjacent to the top surface of said flange for preventing said tab member from moving after said flange is in contact said seat, whereby said needle cover cannot be removed without damaging said shield once said flange is in contact with said seat.

4. The invention as set forth in 1 wherein said protective shield has a first annular reinforcing portion near said central opening, and a second annular reinforcing portion at the outer perimeter of said protective shield.

5. The invention as set forth in claim 4 wherein said first annular reinforcing portion has an inside diameter which corresponds to the exterior diameter and shape of said needle cover for further increasing the rigidity of said shield with respect to said needle cover.

6. The invention as set forth in claim 4 wherein said second annular reinforcing portion comprises a rim portion extending upward from the planar surface of said shield for confining said needle within said rim portion when said needle is being inserted into said needle cover.

7. The invention as set forth in claim 4 wherein said first reinforcing portion has a series of axial slots and said needle cover has a series of axial protruding which engage with said slots.

8. A protective shield for use with a hypodermic needle comprising:
   a tubular needle cover having an open end for receiving said needle and having a flange near the open end;
   a generally planar and rigid shield means having a central opening for receiving said tubular needle cover, and having a planar surface perpendicular to the longitudinal axis of said tubular needle cover;
   a rim means attached to said shield means and surrounding said central opening for preventing said hypodermic needle from sliding off the edge of said shield means, and
   means for permanently fastening said flange within said central opening when said tubular needle cover is inserted into said central opening comprising
   a portion of said central opening having a smaller diameter than said flange, wherein said planar surface forms a seat that contacts the bottom surface of said flange when said needle cover is inserted into said central opening; and
   at least one flexible tab member extending from said planar surface partially over said central opening, for engaging the top surface of the flange when the bottom surface of the flange is positioned over said seat;
   said flexible tab member having an angled portion which contacts the bottom of said central opening for facilitating bending of said tab member;
   said tab member also having a flat surface parallel and adjacent to the tope surface of said flange for preventing said tab member from bending after said flange is in contact with said seat, whereby said needle cover cannot be removed without damaging said shield once said flange is in contact with said seat.

9. The invention as set forth in claim 8 wherein said shield is generally disc-shaped and has a first annular reinforcing portion at the central opening and a second annular reinforcing portion at the outer perimeter.

10. The invention as set forth in claim 8 wherein said first annular reinforcing portion has an inside diameter which corresponds to the exterior diameter and shape of said needle cover for further increasing the rigidity of said shield with respect to said needle cover.

11. The invention as set forth in claim 8 further comprising a series of protruding portions extending radially outward from the perimeter of said shield for preventing said shield from rolling when placed on a flat surface.

12. A protective shield for use with a hypodermic needle comprising:
   a tubular needle cover having an open end for receiving said needle and having a flange near the open end;
   a generally planar and rigid shield means having a central opening for receiving said tubular needle cover, and having a planar surface perpendicular to the longitudinal axis of the tubular needle cover;
   means for permanently fastening said flange with said central opening comprising a portion of said central opening having a smaller diameter than said flange, wherein the bottom of said planar surface forms a seat that contacts the bottom surface of said flange when said needle cover is inserted into said central opening, and at least one flexible tab member extending from the perimeter of said first portion of the central opening over said central opening, for engaging the top surface of the flange when the bottom surface of the flange is in contact with said seat, said flexible tab member having an angled portion which contacts said flange portion while said needle cover is being inserted into said central opening for facilitating movement of said tab member, said tab member also having a flat surface parallel and adjacent to the top surface of said flange for preventing said tab member from bending after said flange is in contact with said seat, whereby said needle cover cannot be removed without damaging said shield once said flange is in contact with said seat; and
   rim means attached to said shield means and surrounding said central opening for preventing said hypodermic needle from sliding off the edge of said shield means.

* * * * *